US009274086B1

(12) United States Patent
Windsor et al.

(10) Patent No.: US 9,274,086 B1
(45) Date of Patent: Mar. 1, 2016

(54) MAGNETIC SHIELDING OF SERVO-MOTORS IN MAGNETIC DETECTION SYSTEMS

(75) Inventors: George Burton Windsor, Gig Harbor, WA (US); Frank Edward Hudik, Yelm, WA (US); Joseph John Natale, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 1096 days.

(21) Appl. No.: 13/278,729

(22) Filed: Oct. 21, 2011

(51) Int. Cl.
  *G01N 27/72* (2006.01)
  *G01N 27/90* (2006.01)

(52) U.S. Cl.
  CPC ........ *G01N 27/9046* (2013.01); *G01N 27/9093* (2013.01)

(58) Field of Classification Search
  CPC .......... G01N 27/9046; G01N 27/9093; G01N 27/9033; G01N 27/902; G01N 27/9013; G01N 27/904; G01R 1/18; G01R 1/07342; G01R 1/06711; G01R 1/06772; G01R 1/04; G01R 31/2886; G01R 31/2889
  USPC ............ 324/226, 201, 219, 260, 262, 750.26, 324/750.27
  See application file for complete search history.

(56) References Cited

U.S. PATENT DOCUMENTS

| | | | |
|---|---|---|---|
| 4,665,870 A | 5/1987 | Cerini et al. | |
| 6,163,148 A * | 12/2000 | Takada | B62M 6/45 180/206.3 |
| 6,333,631 B1 * | 12/2001 | Das | F41H 11/12 250/392 |
| 6,731,968 B2 * | 5/2004 | Buchanan | 600/409 |
| 6,791,329 B2 * | 9/2004 | Nelson | 324/329 |
| 7,061,390 B2 * | 6/2006 | Murata | 340/686.1 |
| 7,559,385 B1 * | 7/2009 | Burt | B60K 7/0007 180/167 |
| 7,902,700 B1 * | 3/2011 | Gabrys | H02K 1/27 310/156.83 |
| 2004/0104632 A1 * | 6/2004 | Keene | H02K 16/00 310/85 |
| 2006/0119026 A1 * | 6/2006 | Ryaboy et al. | 267/140.15 |
| 2011/0175604 A1 * | 7/2011 | Polzer et al. | 324/246 |

OTHER PUBLICATIONS

Magnetic Shield Corp, MuMetal Data; http://www.magnetic-shield.com/products/mumetal.html; ©1997-2010.
MuShield, Design & Fabrication Solutions for a Wide Range of Applications; http://www.mushield.com/shielding.shtml; ©1996-2011.
International Application Status Report for PCT Publication WO2002/041474; Publication Date May 23, 2002; Report Generated Mar. 17, 2010.

* cited by examiner

*Primary Examiner* — Tung X Nguyen
*Assistant Examiner* — Thang Le

(57) ABSTRACT

A magnetic detection system includes a platform, a magnetic detection sensor, a servo-motor, and a magnetic shield. The platform is an unmanned platform. The magnetic anomaly detection sensor is located onboard the unmanned platform. The servo-motor is also located onboard the unmanned platform. The magnetic shield is further disposed onboard the unmanned platform over the servo-motor reducing magnetic noise the magnetic anomaly detection sensor receives from the servo-motor.

25 Claims, 5 Drawing Sheets

MAGNETIC SHIELDING OF SERVO-MOTORS IN MAGNETIC DETECTION SYSTEMS

FIELD OF THE DISCLOSURE

The disclosure relates to apparatus and methods for shielding servo-motors in magnetic detection systems.

BACKGROUND OF THE DISCLOSURE

Servo-motors of magnetic detection systems produce magnetic noise, such as magnetic moment, which may interfere with magnetic detection sensors of the magnetic detection systems. Magnetic detection sensors require a minimum threshold signal-to-noise ratio to be operationally effective. In unmanned air vehicles the magnetic noise produced by servo-motors may interfere with magnetic anomaly detection sensors searching the environment below for magnetic anomalies. This may lead to the magnetic anomaly detection sensors taking inaccurate readings. Some of the existing unmanned air vehicles attempt to resolve this issue by towing the magnetic anomaly detection sensors behind the platform upon which the servo-motor is located to increase the distance between the servo-motor and the magnetic anomaly detection sensors thereby decreasing the amount of magnetic noise the magnetic anomaly detection sensors receive from the servo-motor. However, this causes an increase in cost, size, and the possibility of detection of the unmanned air vehicle by an enemy.

A magnetic detection system and method is needed to overcome one or more issues of the existing magnetic detection systems and methods.

SUMMARY OF THE DISCLOSURE

In one embodiment, a magnetic detection system is disclosed. The magnetic detection system comprises a platform, a magnetic detection sensor, a servo-motor, and a magnetic shield. The platform is an unmanned platform. The magnetic anomaly detection sensor is located onboard the unmanned platform. The servo-motor is also located onboard the unmanned platform. The magnetic shield is further disposed onboard the unmanned platform over the servo-motor reducing magnetic noise the magnetic anomaly detection sensor receives from the servo-motor.

In another embodiment, a magnetic shield assembly is disclosed. The magnetic shield assembly comprise a first magnetic shield portion detachably mated to a second magnetic shield portion forming a cavity between the first magnetic shield portion and the second magnetic shield portion. The first and second magnetic shield portions have a relative magnetic permeability in a range of 1 to 100,000. The first and second magnetic shield portions are configured to, when magnetic moment in a range of 25 nT-ft$^3$ to 96.4 nT-ft$^3$ is emulating from within the cavity, to reduce magnetic noise from traveling outside the cavity by a factor in a range of 234 to 1,060.

In an additional embodiment, a method of reducing magnetic noise is disclosed. In one step, a servo-motor is shielded with a magnetic shield onboard an unmanned platform. In another step, magnetic noise emitted by the servo-motor is reduced due to the magnetic shield.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
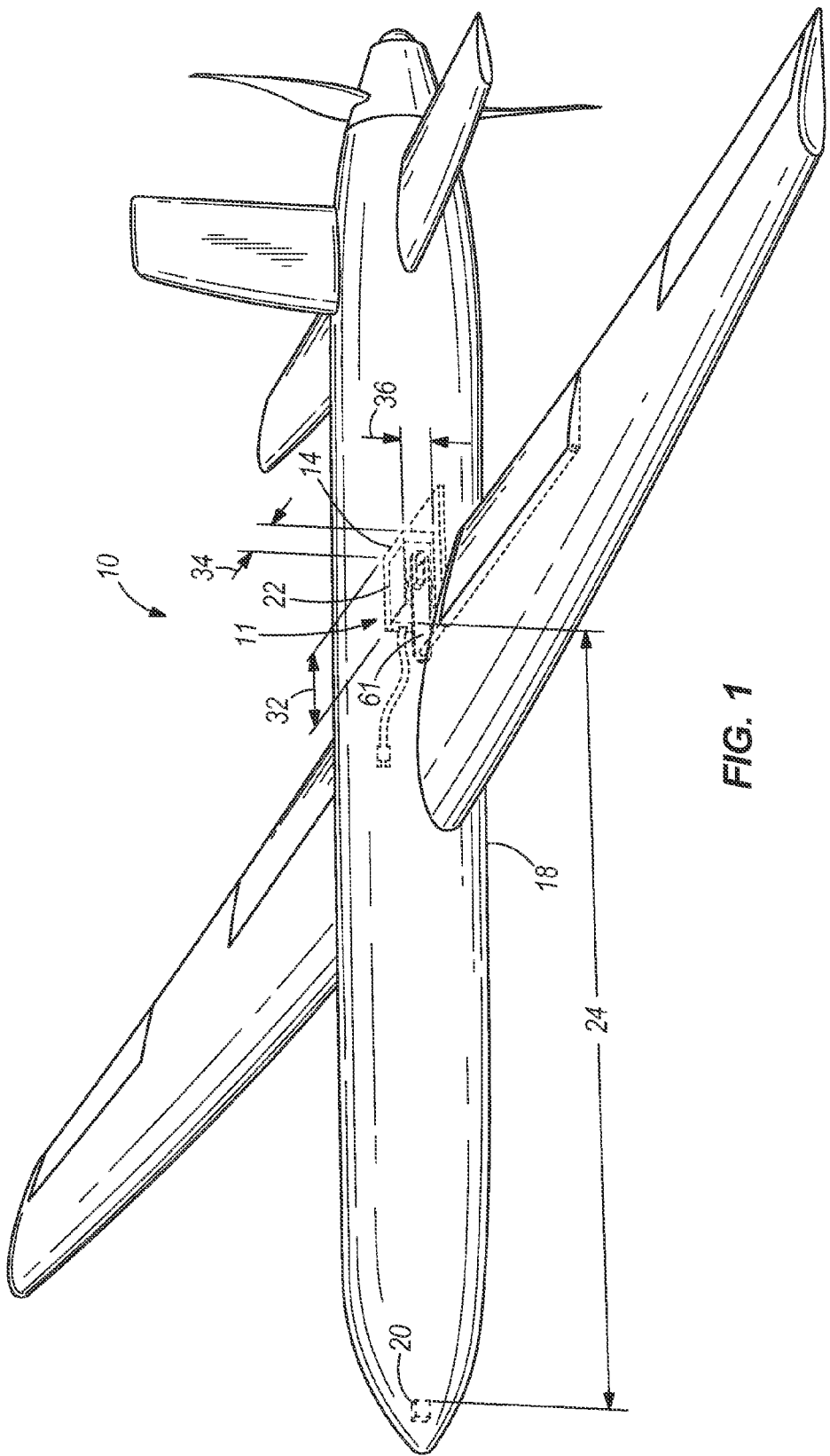
FIG. 1 illustrates a top perspective view of one embodiment of a magnetic detection system.
Figure 2:
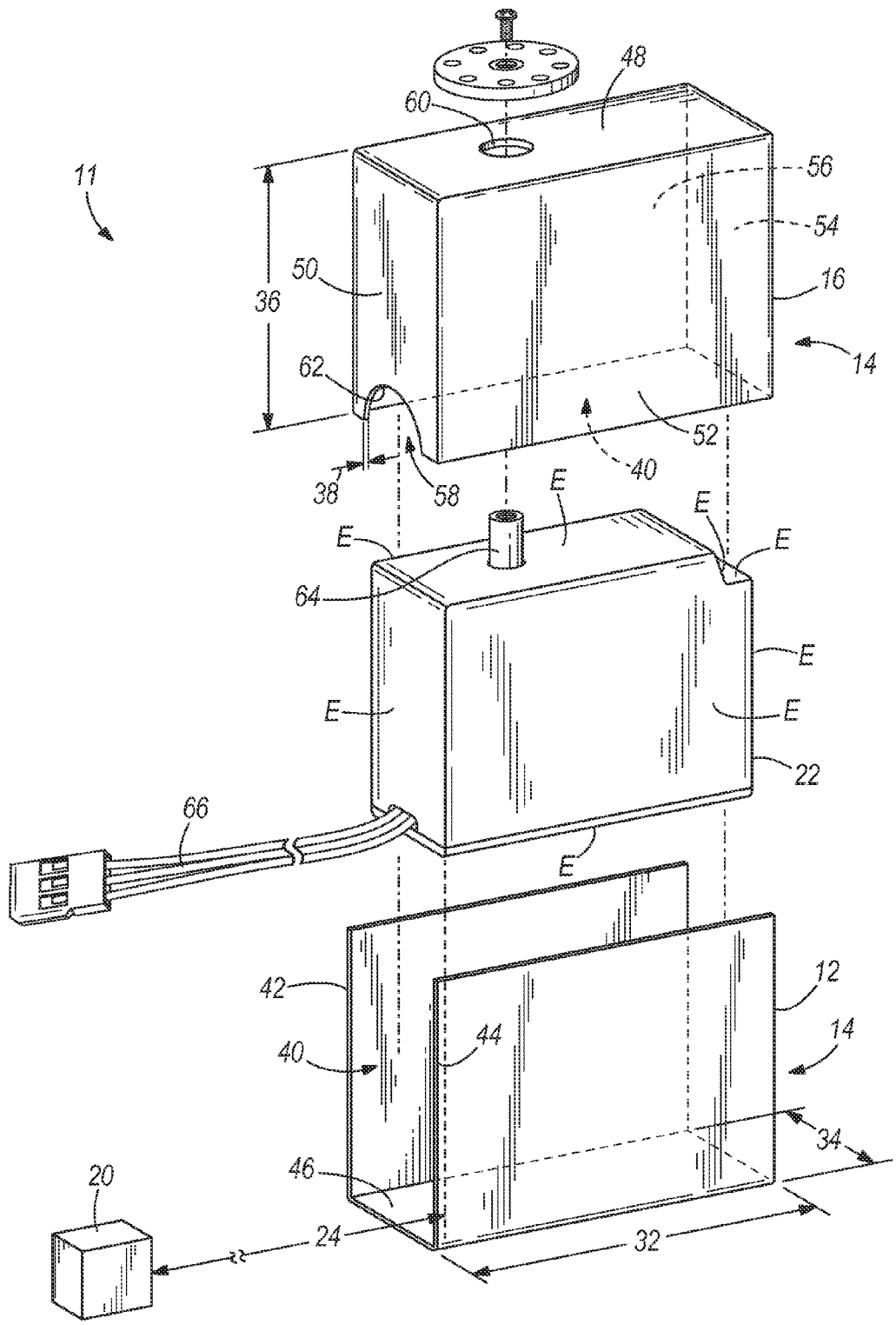
FIG. 2 illustrates a partially disassembled view of a portion of the magnetic detection system of FIG. 1 with a first magnetic shield portion, spaced apart from a magnetic anomaly detection sensor, unmated from a second magnetic shield portion.

FIG. 1 illustrates a top perspective view of one embodiment of a magnetic detection system 10. FIG. 2 illustrates a partially disassembled view of a portion 11 of the magnetic detection system 10 of FIG. 1 with a first magnetic shield portion 12 of a magnetic shield 14 of the magnetic detection system 10, spaced apart from a magnetic anomaly detection sensor 20, unmated from a second magnetic shield portion 16 of the magnetic shield 14. In one embodiment, the magnetic detection system 10 comprises an unmanned magnetic anomaly detection system. In another embodiment, the magnetic detection system 10 may comprise an unmanned autonomously controlled magnetic anomaly detection system. In other embodiments, the magnetic detection system 10 may vary in type.

As shown in FIGS. 1 and 2 collectively, the magnetic detection system 10 includes a platform 18, a magnetic anomaly detection sensor 20, a servo-motor 22, and a magnetic shield 14. In one embodiment, the platform 18 comprises an unmanned air vehicle (UAV). In another embodiment, the platform 18 may comprise varying types of aircraft. In still other embodiments, the platform 18 may vary in type. The magnetic anomaly detection sensor 20 comprises a measuring instrument for measuring the strength or direction of a magnetic field. In one embodiment, the magnetic anomaly detection sensor 20 may be used by a platform 18 comprising a UAV to determine a magnetic anomaly in territory under observation. The magnetic anomaly detection sensor 20 requires a minimum threshold signal-to-noise ratio to be operationally effective. In other embodiments, the magnetic anomaly detection sensor 20 may be used for varying purposes. The magnetic anomaly detection sensor 20 is located onboard the platform 18. In other embodiments, the location of the magnetic anomaly detection sensor 20 may vary.

The servo-motor 22 comprises an electromechanical device used to transform an electrical signal (an input) into a mechanical output (a position). The servo-motor 22 is located onboard the platform 18. In other embodiments, the location of the servo-motor 22 may vary. In the embodiment in which the platform 18 comprises a UAV, the servo-motor 22 is used to transfer electric impulses into motion for the purpose of affecting the vehicle's motion. In other embodiments, the servo-motor 22 may be used for varying purposes. The servo-motor 22 is an inherent source of magnetic noise which interferes with a magnetic anomaly detection sensor 20.

The magnetic shield 14 comprises a magnetically permeable shield for reducing the amount of magnetic noise (i.e. the signature of a magnetic signal) from the servo-motor 22 which reaches the magnetic anomaly detection sensor 20. This prevents the magnetic noise from the servo-motor 22 from interfering with the magnetic anomaly detection sensor 20 to avoid inaccurate readings of the magnetic anomaly detection sensor 20 as a result of the magnetic noise of the servo-motor 22. In order to prevent the amount of magnetic noise produced by the servo-motor 22 from exceeding a threshold level of magnetic noise which will interfere with the accuracy of the magnetic anomaly detection sensor 20, a designer of the magnetic detection system 10 may adjust a number of design components. These adjustable design components are based in part on the amount of magnetic noise produced by the particular servo-motor 22, on the sensitivity of the particular magnetic anomaly detection sensor 20, and on the margin for end-use applications including operating environment considerations.

In one embodiment, the servo-motor 22 produces magnetic moment in a range of 25 nT-ft$^3$ to 96.4 nT-ft$^3$, and the magnetic shield 14 reduces the magnetic noise the magnetic anomaly detection sensor 20 receives from the servo-motor 22 relative to the magnetic noise the magnetic anomaly detection sensor 20 would receive from the servo-motor 22 if the magnetic shield 14 were not present by a factor in a range of 234 to 1,060. In other embodiments, the servo-motor 22 produces magnetic moment in varying ranges, and the magnetic shield 14 reduces the magnetic noise the magnetic anomaly detection sensor 20 receives from the servo-motor 22 in varying amounts.

The adjustable design components include: the location of the magnetic shield 14 and servo-motor 22 relative to one another and relative to the location of the magnetic anomaly detection sensor 20; the configuration (i.e. shape, size, length, width, height, and thickness) of the magnetic shield 14, disposed in-between the servo-motor 22 and the magnetic anomaly detection sensor 20, shielding the servo-motor 22; and the magnetic permeability of the magnetic shield 14.

In one embodiment, as shown in FIGS. 1 and 2 collectively, the magnetic shield 14 is disposed onboard the platform 18 over and substantially encasing the servo-motor 22, in-between the servo-motor 22 and the magnetic anomaly detection sensor 20, reducing the amount of the magnetic noise the magnetic anomaly detection sensor 20 receives from the servo-motor 22. The closest distance 24 between the servo-motor 22 and the magnetic anomaly detection sensor 20 is chosen to prevent the amount of magnetic noise produced by the servo-motor 22 from exceeding the threshold level of magnetic noise which will interfere with the accuracy of the magnetic anomaly detection sensor 20. The larger the distance 24 is, the more the magnetic noise, produced by the servo-motor 22 and reaching the magnetic anomaly detection sensor 20, is reduced. In one embodiment, the distance 24 is in a range of 0 to 72 inches. In other embodiments, these distances may vary.

The configuration (i.e. shape, size, length, width, height, and thickness) of the magnetic shield 14, relative to the servo-motor 22 and to the magnetic anomaly detection sensor 20, may also be chosen to prevent the amount of magnetic noise produced by the servo-motor 22 from exceeding the threshold level of magnetic noise which will interfere with the accuracy of the magnetic anomaly detection sensor 20. The more the magnetic shield 14 encases (i.e. encloses) all surfaces of the servo-motor 22 to further magnetically separate them from the magnetic anomaly detection sensor 20, by adjusting the shape, length 32, width 34, height 36, and thickness 38 of the magnetic shield 14, the more the magnetic noise produced by the servo-motor 22 will be reduced prior to reaching the magnetic anomaly detection sensor 20. In one embodiment, the shape of the magnetic shield 14 is a six-sided rectangle and the servo-motor 22 is enclosed within a cavity 40 of the magnetic shield 14. In other embodiments the shape of the magnetic shield 14 may be a spheroid, a circle, or another shape. In one embodiment, the length 32 may be in a range of 0.5 to 4.0 inches; the width 34 may be in a range of 0.5 to 4.0 inches; the height 36 may be in a range of 0.5 to 4.0 inches; and the thickness 38 may be in a range of 0.004 to 0.1 inches. In other embodiments, the length 32, width 34, height 36, and thickness 38 may vary.

In one embodiment, as shown in FIGS. 1 and 2 collectively, the magnetic shield 14 comprises a first magnetic shield portion 12 and a second magnetic shield portion 16 adapted to mate and unmate from one another to form the six-sided rectangle having the cavity 40 enclosing the servo-motor 22. The first magnetic shield portion 12 comprises a three-sided U-shape comprising attached surfaces 42, 44, and 46. Surface 46 extends perpendicularly between parallel surfaces 42 and 44. In other embodiments, the first magnetic shield portion 12 may comprise three to five sides or other varying shapes of differing sizes. The second magnetic shield portion 16 comprises a substantially rectangular shape having five attached surfaces 48, 50, 52, 54, and 56 and an open end 58. Surfaces 50, 52, 54, and 56 extend perpendicularly from surface 48. Surfaces 50 and 54 are parallel to one another and are disposed perpendicularly relative to parallel surfaces 52 and 56.

Opening 60 is disposed through surface 48 into cavity 40. Opening 62 is disposed through surface 50 into cavity 40. The openings 60 and 62 are disposed in a surface area range of 10 to 20 percent of the collective exterior surfaces 46, 48, 50, 52, 54, and 56 of the magnetic shield 14 with the remaining 80 to 90 percent of the collective exterior surface areas 46, 48, 50, 52, 54, and 56 of the magnetic shield 14 being closed. In other embodiments, the second magnetic shield portion 16 may comprise three to five sides or other varying shapes of differing sizes and having a varying number of openings in varied locations, orientations, or configurations. In additional embodiments, the magnetic shield 14 may comprise a varying number of magnetic shield portions of differing shapes, sizes, orientations, and configurations.

A shaft 64 of the servo-motor 22 extends from within the cavity 40, through the opening 60 in surface 48, and outside of surface 48. The shaft 64 is used to transfer mechanical motion from the servo-motor 22 to an actuating arm 61 which may be used to drive various components of the platform 18 of the magnetic detection system 10. One or more connection members 66 extend from the servo-motor 22 within the cavity 40, through the opening 62 in surface 50, and outside of surface 50. The one or more connection members 66 may comprise one or more electrical wires attached between the servo-motor 22 and other components of the magnetic detection system 10.

The higher the percentage of the collective external surfaces E of the servo-motor 22 the magnetic shield 14 covers, the more the magnetic noise, produced by the servo-motor 22 and reaching the magnetic anomaly detection sensor 20, is reduced. In one embodiment, the magnetic shield 14 covers in a range of 80 to 90 percent of the surface areas of the collective external surfaces E of the servo-motor 22 and does not cover in a range of 10 to 20 percent of the surface areas of the collective external surfaces E of the servo-motor 22. In other embodiments, the magnetic shield 14 may cover a varying percentage of the collective external surfaces E of the servo-motor 22.

Figure 3:
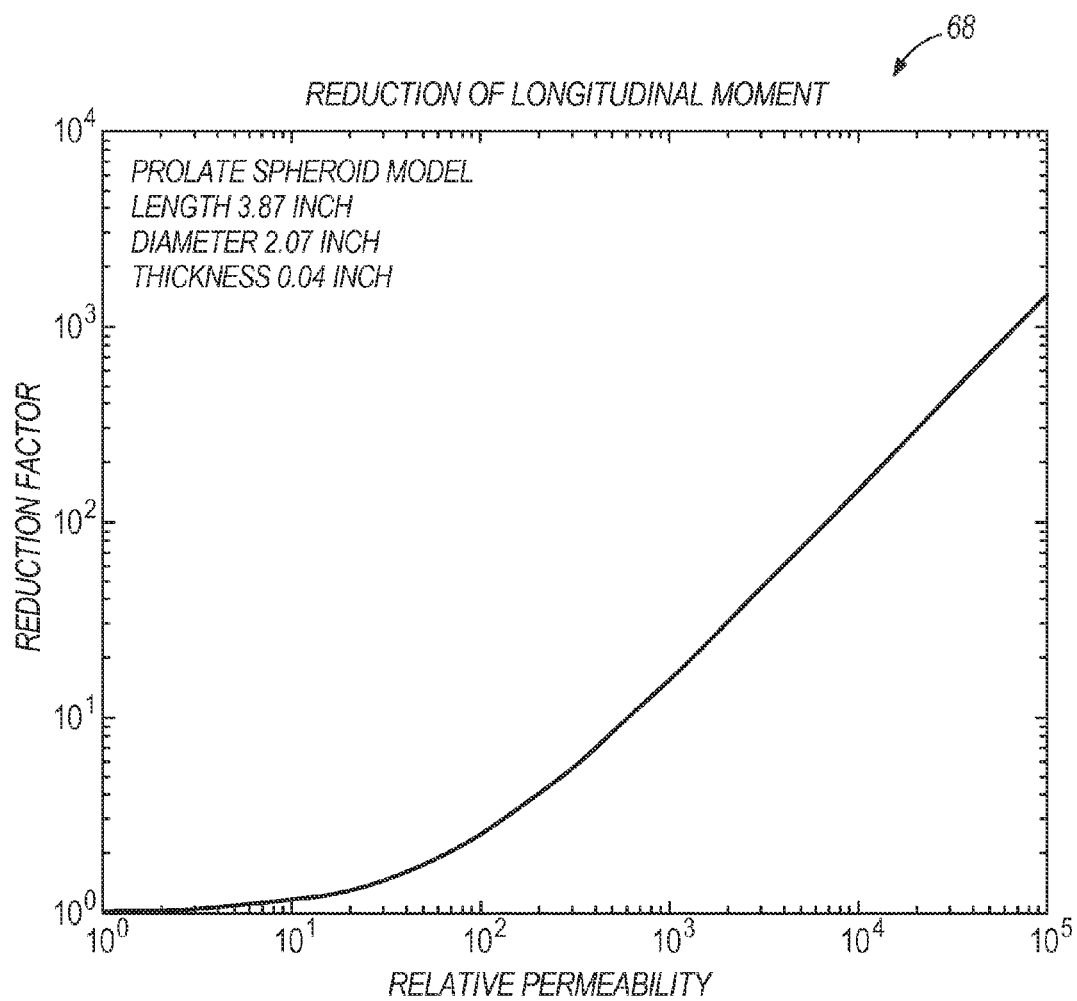
FIG. 3 illustrates a graph plotting magnetic permeability relative to magnetic noise reduction for one embodiment in which a prolate spheroid magnetic shield was used to shield a servo-motor.

The magnetic shield 14 is made of a material having a magnetic permeability configured to reduce the magnetic noise the magnetic anomaly detection sensor 20 receives from the servo-motor 22 in order to prevent the amount of magnetic noise produced by the servo-motor 22 from exceeding the threshold level of magnetic noise which will interfere with the accuracy of the magnetic anomaly detection sensor 20. FIG. 3 illustrates an exemplary graph 68 plotting magnetic permeability on the x-axis and the magnetic noise reduction factor on the y-axis for an embodiment in which a prolate spheroid magnetic shield, having a length of 3.87 inches, a diameter of 2.07 inches, and a thickness of 0.04 inches, was used to shield a servo-motor using a form-fit without external openings in the magnetic shield. This magnetic shield resulted in a theoretical magnetism reduction factor of approximately 1,400. Other magnetic shields of varied shapes having external openings in the magnetic shields would have lower magnetism reduction factors. As shown in FIG. 3, the magnetic noise reduction factor of magnetic shields increases as their permeability increases. Therefore, a designer of the system 10 may choose a material which has a larger magnetic permeability for the magnetic shield 14 in order to further reduce the magnetic noise the magnetic anomaly detection sensor 20 receives from the servo-motor 22.

In one embodiment, the magnetic shield 14, including the first and second magnetic shield portions 12 and 16, is made of mu-metal. Mu-metal comprises a class of metal alloys that exhibit high relative magnetic permeability above 60,000 which may be used for magnetic shielding to provide attenuation of magnetic noise. In one embodiment, the mu-metal comprises varying percentages of nickel, iron, copper, and molybdenum. The mu-metal may comprise in a range of 60 to 80 percent nickel; in a range of 10 to 20 percent iron; in a range of 5 to 15 percent copper; and in a range of 5 to 15 percent molybdenum. The magnetic shield 14 may be made of a material having a relative magnetic permeability in a range of 1 to 100,000. In other embodiments, the magnetic shield 14 may be made of varying magnetically permeable materials of varying percentages.

Figure 4:
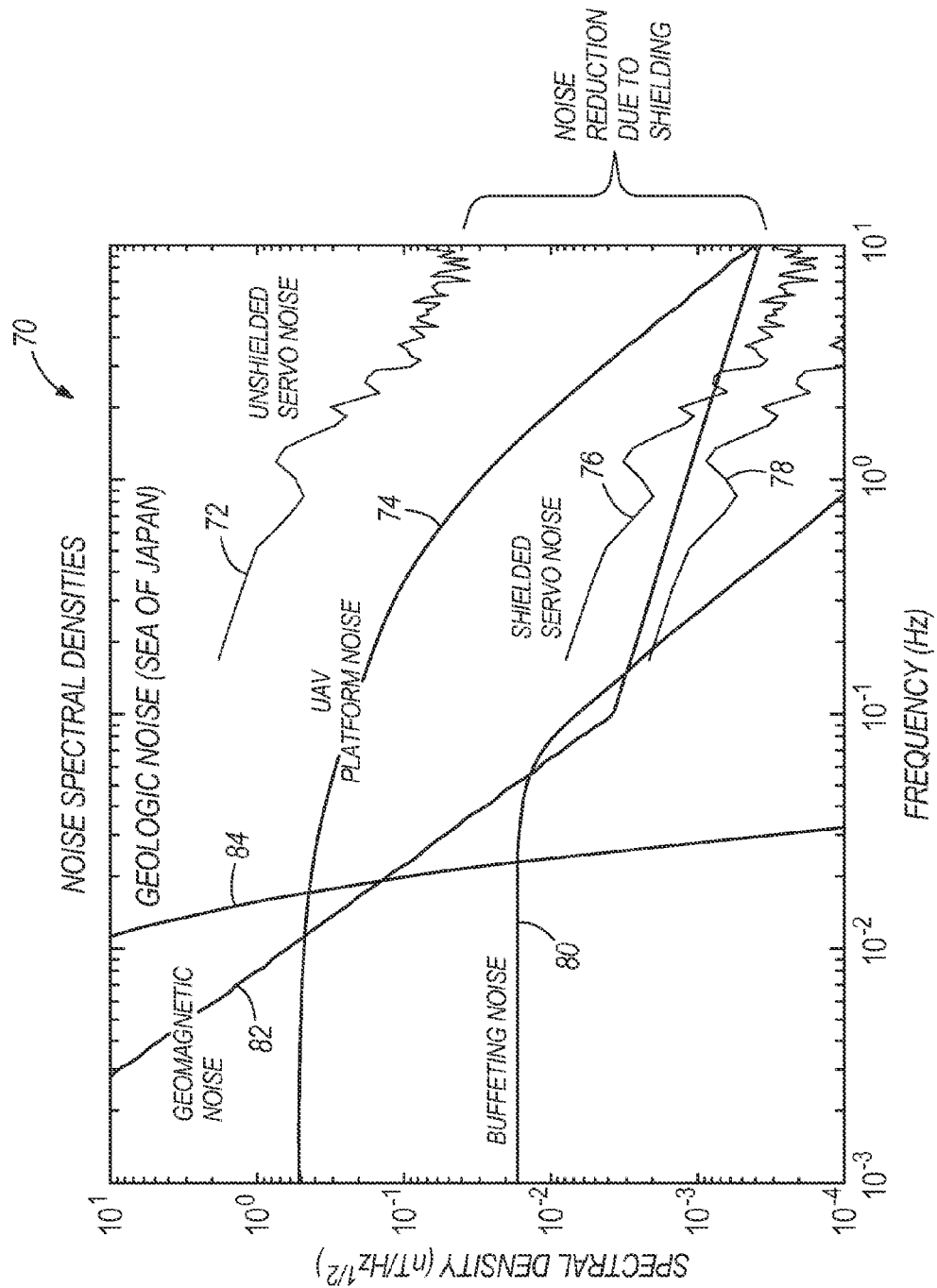
FIG. 4 illustrates a graph plotting frequency relative to spectral density for varying sources of noise.

FIG. 4 illustrates an exemplary graph 70 plotting frequency on the x-axis and spectral density on the y-axis for varying sources of noise. Curve 72 represents, for one embodiment, the amount of magnetic noise received by a magnetic anomaly detection sensor from a servo-motor which was not shielded by a magnetic shield. Curve 72 exceeds the magnetic noise threshold curve 74 for a UAV platform at which a magnetic anomaly detection sensor will operate accurately. Curve 76 represents, for another embodiment, the amount of magnetic noise received by a magnetic anomaly detection sensor which was shielded from one-type of servo-motor by a magnetic shield. Curve 76 is below the magnetic noise threshold curve 74 for the UAV platform and has a magnetic noise reduction factor in excess of 234 relative to the magnetic noise produced by curve 72. Curve 78 represents, for still another embodiment, the amount of magnetic noise received by a magnetic anomaly detection sensor which was shielded from another type of servo-motor by a magnetic shield. Curve 78 is below the magnetic noise threshold curve 74 for the UAV platform and has a magnetic noise reduction factor in excess of 881 relative to the magnetic noise produced by curve 72. The difference in curves 76 and 78 resulted due to the varied input signal types (varied waveform shapes) of the differing servo-motors tested, and due to practical design constraints such as penetrations for wires and mechanical linkages. For comparison purposes, curves 80, 82, and 84 respectively represent the amounts of buffeting noise, geomagnetic noise, and geologic noise.

Figure 5:
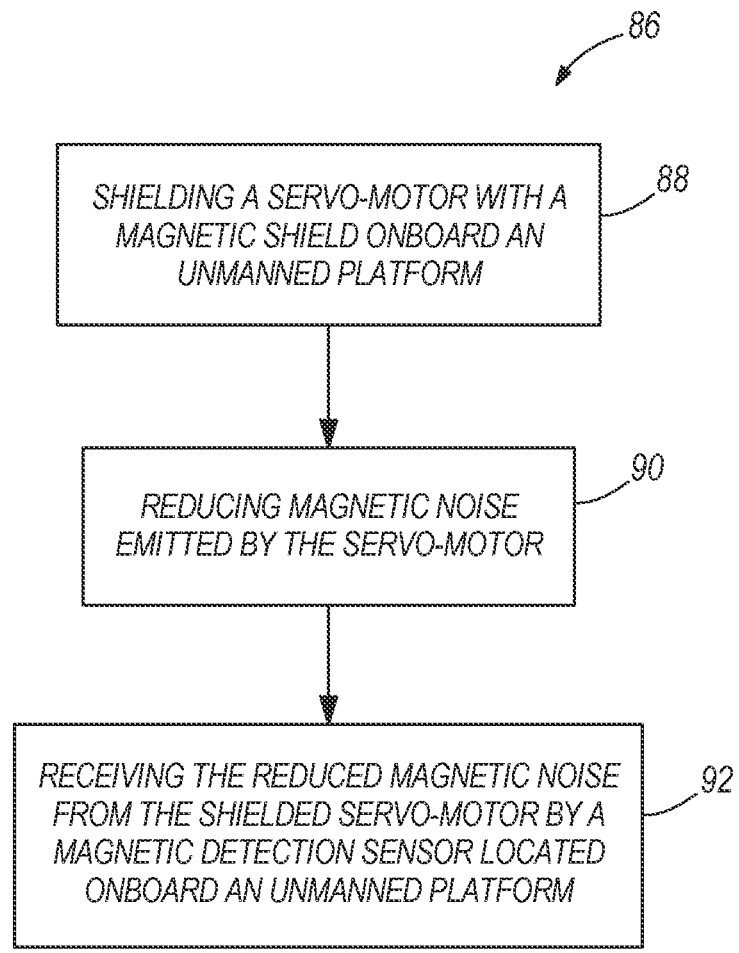
FIG. 5 illustrates a flowchart illustrating one embodiment of a method of reducing magnetic noise.

FIG. 5 illustrates a flowchart 86 illustrating one embodiment of a method of reducing magnetic noise. In step 88, a servo-motor is shielded with a magnetic shield onboard an unmanned platform. The magnetic shield may have a relative magnetic permeability in a range of 1 to 100,000. In one embodiment, step 88 comprises mating a first magnetic shield portion of the magnetic shield to a second magnetic shield portion of the magnetic shield to dispose the servo-motor within a cavity between the first and second magnetic shield portions. In another embodiment, step 88 comprises extending at least a portion of the servo-motor through at least one opening in the magnetic shield. In step 90, magnetic noise emitted by the servo-motor is reduced due to the magnetic shield. In one embodiment, in step 90 the servo-motor emits magnetic moment in a range of 25 nT-ft$^3$ to 96.4 nT-ft$^3$ and the magnetic shield reduces the magnetic noise, emitted by the servo-motor, traveling beyond the magnetic shield by a factor in a range of 234 to 1,060. In step 92, the magnetic noise, from the servo-motor, received by a magnetic anomaly detection sensor located onboard the unmanned platform is reduced due to the magnetic shield. In one embodiment, in step 92 the magnetic noise, from the servo-motor, received by a magnetic anomaly detection sensor located onboard the unmanned platform is reduced by a factor in the range of 234 to 1,060 due to the magnetic shield.

One or more embodiments of the disclosure reduce one or more issues experienced by the existing magnetic detection systems and methods by using a magnetic shield to reduce the magnetic noise, emulating from a servo-motor, which is received by a magnetic detection sensor. This avoids having to tow the magnetic anomaly detection sensor a large distance behind the platform upon which the servo-motor is located which reduces cost, size, and the possibility of detection of the unmanned air vehicle by an enemy.

It should be understood, of course, that the foregoing relates to exemplary embodiments of the disclosure and those modifications may be made without departing from the spirit and scope of the disclosure as set forth in the following claims.

We claim:

1. A magnetic detection system, comprising:
an unmanned platform;
a magnetic anomaly detection sensor located onboard the unmanned platform;
a servo-motor including collective external surfaces and located onboard the unmanned platform; and
a magnetic shield disposed onboard the unmanned platform to enclose or to substantially enclose the servo-motor and to reduce magnetic noise that the magnetic anomaly detection sensor receives from the servo-motor,
wherein the magnetic shield comprises first and second magnetic shield portions detachably mated together, wherein the collective external surfaces are disposed substantially within a first cavity formed by the first magnetic shield portion, and the collective external surfaces are disposed substantially within a second cavity formed by the second magnetic shield portion.

2. The magnetic detection system of claim 1, wherein the servo-motor emits magnetic moment in a range of 25 nT-ft$^3$ to 96.4 nT-ft$^3$, and the magnetic shield reduces the magnetic noise that the magnetic anomaly detection sensor receives from the servo-motor by a factor in a range of 234 to 1,060.

3. The magnetic detection system of claim 1, wherein the magnetic shield is configured so that the magnetic noise that the magnetic anomaly detection sensor receives from the servo-motor is less than a magnetic noise threshold.

4. The magnetic detection system of claim 1, wherein the magnetic anomaly detection sensor is located in a range of 0 to 72 inches away from the servo-motor.

5. The magnetic detection system of claim 1, wherein the magnetic shield is made of a material having a relative magnetic permeability in a range of 1 to 100,000.

6. The magnetic detection system of claim 5, wherein the magnetic shield is made of mu-metal comprising nickel, iron, copper, and molybdenum.

7. The magnetic detection system of claim 6, wherein the mu-metal comprises in a range of 60 to 80 percent nickel, in a range of 10 to 20 percent iron, in a range of 5 to 15 percent copper, and in a range of 5 to 15 percent molybdenum.

8. The magnetic detection system of claim 1, wherein the magnetic shield covers in a range of 80 to 90 percent of surface areas of collective external surfaces of the servo-motor.

9. The magnetic detection system of claim 1, wherein the mated first and second magnetic shield portions collectively form a six-sided rectangular prism.

10. The magnetic detection system of claim 1, wherein the magnetic shield comprises at least one opening through which a portion of the servo-motor protrudes from within the first cavity of the magnetic shield to outside of the magnetic shield.

11. The magnetic detection system of claim 1, wherein the magnetic shield is sized to enclose the servo-motor within the magnetic shield.

12. The magnetic detection system of claim 1, wherein the unmanned platform comprises an unmanned vehicle and the magnetic anomaly detection sensor detects a magnetic anomaly in a territory outside the unmanned vehicle which is under observation.

13. The magnetic detection system of claim 1, wherein the unmanned platform comprises an aircraft.

14. A magnetic detection system, comprising:
an unmanned vehicle;
a magnetic shield assembly, attached to the unmanned vehicle, comprising:
a first magnetic shield portion detachably mated to a second magnetic shield portion and the first magnetic field portion forming a first cavity, within which a servo motor is disposed, between the first magnetic shield portion and the second magnetic shield portion, wherein the first and second magnetic shield portions have a relative magnetic permeability in a range of 1 to 100,000 and when magnetic moment emulating from the servo motor in the first cavity is in a range of 25 nT-ft$^3$ to 96.4 nT-ft$^3$ reduce noise traveling outside the first cavity by a factor of 234 to 1,060, wherein the second magnetic shield portion forms a second cavity within which the servo-motor is also disposed; and
a magnetic anomaly detection sensor, attached to the unmanned vehicle, which detects a magnetic anomaly in a territory outside the unmanned vehicle which is under observation.

15. The magnetic detection system of claim 14, wherein the mated first and second magnetic shield portions collectively form a six-sided rectangular prism.

16. The magnetic detection system of claim 15, wherein each of the mated first and second magnetic shield portions comprise three to five sided shapes.

17. The magnetic detection system of claim 15, wherein the six-sided rectangle comprises one or more openings extending from outside the six-sided rectangle to within the cavity of the six-sided rectangle, with a surface area range of 10 to 20 percent of collective external surfaces of the six-sided rectangle having the one or more openings and the remainder of the collective external surfaces of the six-sided rectangle being closed.

18. The magnetic detection system of claim 14, wherein the first and second magnetic shield portions are made of mu-metal having a range of 60 to 80 percent nickel, a range of 10 to 20 percent iron, a range of 5 to 15 percent copper, and a range of 5 to 15 percent molybdenum.

19. The magnetic detection system of claim 14, wherein the magnetic shield assembly comprises a height in a range of 0.5 to 4.0 inches, a width in a range of 0.5 to 4.0 inches, a length in a range of 0.5 to 4.0 inches, and a thickness in a range of 0.004 to 0.1 inches.

20. A method of reducing magnetic noise, comprising:
shielding collective external surfaces of a servo-motor with a magnetic shield onboard an unmanned platform, wherein the shielding comprises mating a first magnetic shield portion of the magnetic shield to a second magnetic shield portion of the magnetic shield to dispose the servo-motor within a first cavity between the first and second magnetic shield portions, wherein the collective external surfaces are disposed substantially within a first cavity formed by the first magnetic shield portion, and the collective external surfaces are disposed substantially within a second cavity formed by the second magnetic shield portion; and
reducing magnetic noise emitted by the servo-motor and received by a magnetic anomaly detection sensor due to the magnetic shield.

21. The method of claim 20, wherein the servo-motor, the magnetic shield, and the magnetic anomaly detection sensor are attached to an unmanned vehicle, and further comprising detecting a magnetic anomaly in a territory outside the unmanned vehicle with the magnetic anomaly detection sensor.

22. The method of claim 20, further comprising extending at least a portion of the servo-motor through at least one opening in the magnetic shield.

23. The method of claim 20, wherein the magnetic shield is made of a material having a relative magnetic permeability in a range of 1 to 100,000.

24. The method of claim 23, further comprising the servo-motor emitting the magnetic moment in a range of 25 nT-ft$^3$ to 96.4 nT-ft$^3$, and the magnetic shield reducing the magnetic noise, emitted by the servo-motor, traveling beyond the magnetic shield by a factor in a range of 234 to 1,060.

25. The method of claim 20, wherein the unmanned platform comprises an aircraft.

* * * * *